US012788857B2

(12) United States Patent
Linehan

(10) Patent No.: US 12,788,857 B2
(45) Date of Patent: Nov. 10, 2026

(54) DUAL LUMEN DRAINAGE CANNULA WITH INTERNAL FLOW RESTRICTOR

(71) Applicant: CardiacAssist, Inc., Pittsburgh, PA (US)

(72) Inventor: Michael J. Linehan, Narberth, PA (US)

(73) Assignee: CardiacAssist, Inc.

(*) Notice: Subject to any disclaimer, the term of this patent is extended or adjusted under 35 U.S.C. 154(b) by 228 days.

(21) Appl. No.: 17/582,708

(22) Filed: Jan. 24, 2022

(65) Prior Publication Data

US 2023/0233746 A1 Jul. 27, 2023

(51) Int. Cl.
*A61M 1/16* (2006.01)
*A61M 1/26* (2006.01)
*A61M 1/36* (2006.01)

(52) U.S. Cl.
CPC .......... *A61M 1/1698* (2013.01); *A61M 1/267* (2014.02); *A61M 1/3659* (2014.02); *A61M 1/3666* (2013.01); *A61M 2205/3334* (2013.01)

(58) Field of Classification Search
CPC .. A61M 1/1698; A61M 1/267; A61M 1/3659; A61M 1/28; A61M 1/3666; A61M 2205/3334
See application file for complete search history.

(56) References Cited

U.S. PATENT DOCUMENTS 3,851,646 A 12/1974 Sams
3,902,492 A 9/1975 Greenhalgh
4,248,224 A 2/1981 Jones
4,309,994 A 1/1982 Grunwald
4,804,359 A 2/1989 Grunwald et al.
5,476,453 A 12/1995 Mehta
5,584,803 A 12/1996 Stevens et al.
5,609,627 A 3/1997 Goicoechea et al.
5,613,980 A 3/1997 Chauhan
5,702,368 A 12/1997 Stevens et al.
5,720,735 A 2/1998 Dorros
5,769,812 A 6/1998 Stevens et al.
5,785,686 A 7/1998 Runge
5,792,094 A 8/1998 Stevens
(Continued)

FOREIGN PATENT DOCUMENTS

WO WO-2016119771 A2 * 8/2016 .......... A61M 1/1008
WO 2021173486 A1 9/2021

*Primary Examiner* — Rebecca E Eisenberg
*Assistant Examiner* — Kate Elizabeth Strachan
(74) *Attorney, Agent, or Firm* — Seager, Tufte & Wickhem LLP

(57) ABSTRACT

A dual lumen drainage cannula configured for use in a veno-arterial extracorporeal membrane oxygenation (VA ECMO) system includes a first drainage tube having a proximal end, a distal end, and at least one aperture defined proximate its distal end and in fluid communication with the lumen of the first drainage tube, and a second drainage tube having a proximal end, a distal end, and at least one aperture defined proximate its distal end and in fluid communication with the lumen of the second drainage tube. The dual lumen drainage cannula further includes a flow restrictor disposed within the lumen of at least one of the first and second drainage tubes, configured to adjust the flow distribution of blood flow through the lumens of the first and second drainage tubes.

19 Claims, 7 Drawing Sheets

(56) References Cited

U.S. PATENT DOCUMENTS

| | | | |
|---|---|---|---|
| 5,885,238 | A | 3/1999 | Stevens et al. |
| 5,916,193 | A | 6/1999 | Stevens et al. |
| 5,928,181 | A | 7/1999 | Coleman et al. |
| 5,957,879 | A | 9/1999 | Roberts et al. |
| 6,110,145 | A | 8/2000 | Macoviak |
| 6,117,117 | A | 9/2000 | Mauch |
| 6,152,141 | A | 11/2000 | Stevens et al. |
| 6,161,547 | A | 12/2000 | Barbut |
| 6,190,357 | B1 | 2/2001 | Ferrari et al. |
| 6,210,363 | B1 | 4/2001 | Esch et al. |
| 6,210,380 | B1 | 4/2001 | Mauch |
| 6,258,073 | B1 | 7/2001 | Mauch |
| 6,267,751 | B1 | 7/2001 | Mangosong |
| 6,432,136 | B1 | 8/2002 | Weiss et al. |
| 6,461,327 | B1 | 10/2002 | Addis et al. |
| 6,475,208 | B2 | 11/2002 | Mauch |
| 6,494,875 | B1 | 12/2002 | Mauch |
| 6,508,777 | B1 | 1/2003 | Macoviak et al. |
| 6,582,388 | B1 | 6/2003 | Coleman et al. |
| 6,673,040 | B1 | 1/2004 | Samson et al. |
| 6,682,499 | B2 | 1/2004 | Lenker |
| 6,692,473 | B2 | 2/2004 | St. Cyr |
| 6,726,651 | B1 | 4/2004 | Robinson et al. |
| 6,758,836 | B2 | 7/2004 | Zawacki |
| 6,814,713 | B2 | 11/2004 | Aboul-Hosn et al. |
| 6,837,864 | B1 | 1/2005 | Bertolero et al. |
| 6,878,140 | B2 | 4/2005 | Barbut |
| 6,889,713 | B2 | 5/2005 | Navis |
| 6,902,556 | B2 | 6/2005 | Grimes et al. |
| 6,913,601 | B2 | 7/2005 | St. Goar et al. |
| 7,022,100 | B1 | 4/2006 | Aboul-Hosn et al. |
| 7,025,756 | B2 | 4/2006 | Frazier et al. |
| 7,090,659 | B2 | 8/2006 | Aboul-Hosn et al. |
| 7,229,429 | B2 | 6/2007 | Martin et al. |
| 7,276,043 | B2 | 10/2007 | Heath et al. |
| 7,445,592 | B2 | 11/2008 | Pecor |
| 7,473,239 | B2 | 1/2009 | Wang et al. |
| 7,513,863 | B2 | 4/2009 | Bolling et al. |
| 7,569,029 | B2 | 8/2009 | Clark |
| 7,575,563 | B2 | 8/2009 | Appling |
| 7,604,621 | B2 | 10/2009 | Eidenschink |
| 7,766,853 | B2 | 8/2010 | Lane |
| 7,785,246 | B2 | 8/2010 | Aboul-Hosn et al. |
| 7,819,856 | B2 | 10/2010 | Bates |
| 7,824,357 | B2 | 11/2010 | Al-Rashdan |
| 7,875,017 | B2 | 1/2011 | Sabbah |
| 7,879,003 | B2 | 2/2011 | Bertolero et al. |
| 7,896,832 | B2 | 3/2011 | Zafirelis et al. |
| 7,935,102 | B2 | 5/2011 | Breznock et al. |
| 7,981,093 | B2 | 7/2011 | Schon et al. |
| 8,029,457 | B2 | 10/2011 | Ash et al. |
| 8,231,519 | B2 | 7/2012 | Reichenbach et al. |
| 9,168,352 | B2 | 10/2015 | Kelly et al. |
| 9,782,534 | B2 | 10/2017 | Kelly et al. |
| 10,279,101 | B2 | 5/2019 | Kelly et al. |
| 2003/0004452 | A1 | 1/2003 | Lenker |
| 2003/0138350 | A1 | 7/2003 | Macoviak et al. |
| 2004/0171997 | A1 | 9/2004 | Wilson et al. |
| 2005/0054990 | A1 | 3/2005 | Graft et al. |
| 2005/0096609 | A1 | 5/2005 | Maginot et al. |
| 2005/0277862 | A1 | 12/2005 | Anand |
| 2005/0279370 | A1 | 12/2005 | Aboul-Hosn et al. |
| 2006/0149187 | A1 | 7/2006 | Bertolero et al. |
| 2006/0184098 | A1 | 8/2006 | Barnitz et al. |
| 2007/0106247 | A1 | 5/2007 | Burnett et al. |
| 2007/0129704 | A1 | 6/2007 | O'Mahony et al. |
| 2007/0167925 | A1 | 7/2007 | Jacqmein |
| 2007/0197998 | A1 | 8/2007 | Itou et al. |
| 2008/0021417 | A1 | 1/2008 | Zawacki et al. |
| 2008/0108975 | A1 | 5/2008 | Appling et al. |
| 2008/0215018 | A1 | 9/2008 | Duffy et al. |
| 2009/0005725 | A1 | 1/2009 | Shorey |
| 2009/0069792 | A1 | 3/2009 | Frey et al. |
| 2009/0076482 | A1 | 3/2009 | Jonkman |
| 2009/0088699 | A1 | 4/2009 | King et al. |
| 2009/0124968 | A1 | 5/2009 | Goshgarian |
| 2009/0163864 | A1 | 6/2009 | Breznock et al. |
| 2009/0204083 | A1 | 8/2009 | O'Donnell et al. |
| 2009/0247927 | A1 | 10/2009 | Clark |
| 2009/0247987 | A1 | 10/2009 | Chevalier, Jr. et al. |
| 2009/0312702 | A1 | 12/2009 | Holman et al. |
| 2010/0004594 | A1 | 1/2010 | Eidenschink |
| 2010/0010442 | A1 | 1/2010 | Shivkumar et al. |
| 2010/0057020 | A1 | 3/2010 | Uretsky |
| 2010/0233282 | A1 | 9/2010 | Mishra |
| 2011/0040241 | A1 | 2/2011 | Wang et al. |
| 2011/0190683 | A1 | 8/2011 | Gellman et al. |
| 2011/0245665 | A1 | 10/2011 | Nentwick |
| 2011/0313341 | A1 | 12/2011 | Kassab |
| 2011/0313401 | A1 | 12/2011 | Ash et al. |
| 2012/0165788 | A1 | 6/2012 | Burnett et al. |
| 2012/0260265 | A1 | 10/2012 | Doganata et al. |
| 2014/0257243 | A1* | 9/2014 | Pruitt ...................... A61L 29/06 604/266 |
| 2016/0206798 | A1* | 7/2016 | Williams .............. A61M 60/50 |
| 2017/0128654 | A1* | 5/2017 | Feld ...................... A61M 25/10 |
| 2018/0228960 | A1* | 8/2018 | Marous, III ........ A61M 60/279 |
| 2018/0272049 | A1* | 9/2018 | Yoon ................... A61M 1/3627 |
| 2019/0255245 | A1 | 8/2019 | Kelly et al. |
| 2020/0147295 | A1* | 5/2020 | Van Niekerk ...... A61M 25/1011 |
| 2020/0268951 | A1* | 8/2020 | Nitzan .................. A61M 25/10 |
| 2020/0269025 | A1 | 8/2020 | Nitzan et al. |
| 2021/0100987 | A1* | 4/2021 | Schultz ..................... A61F 7/12 |
| 2021/0260265 | A1 | 8/2021 | Edwards |
| 2021/0268162 | A1 | 9/2021 | Linehan |
| 2021/0346184 | A1* | 11/2021 | Mauger ............ A61B 17/12036 |
| 2022/0355011 | A1* | 11/2022 | Edwards ............. A61M 1/3659 |

* cited by examiner

DUAL LUMEN DRAINAGE CANNULA WITH INTERNAL FLOW RESTRICTOR

FIELD

The present disclosure generally relates to devices and methods for accessing a patient's heart with a cannula. More specifically, the present disclosure is related to cannula assemblies, systems, and methods of use thereof for medical procedures such as veno-arterial extracorporeal membrane oxygenation.

BACKGROUND

Veno-arterial extracorporeal membrane oxygenation (VA ECMO) is one method for treating right ventricular failure and respiratory failure percutaneously. A VA ECMO procedure draws blood from the right atrium and pumps it through an oxygenator and back into the arterial circulation via the femoral artery. VA ECMO bypasses the lungs and the heart completely, elevating arterial pressure and infusing blood into the arterial system with added oxygen and reduced carbon dioxide. One of the results of this therapy is that the blood that remains in the heart must be pumped by the heart to a higher pressure level in order to be ejected by the left ventricle because the VA ECMO system has elevated the arterial pressure to a higher level that represents a higher afterload to the pumping effort of the left ventricle.

In conventional VA ECMO systems, one drainage cannula is placed in the superior vena cava (SVC), inferior vena cava (IVC), or right atrium region by way of a femoral vein (typically) to drain blood therefrom and a separate, second return cannula is placed in an artery to return oxygenated (and cleansed from carbon dioxide) blood at a higher pressure. To drain additional blood from the pulmonary artery in conventional VA ECMO systems requires the insertion of a second drainage cannula (third total cannula) placed into the pulmonary artery by way of the jugular vein or other access site. Among the benefits of drawing blood from both the right atrium and the pulmonary artery is that the blood drained is fully mixed venous blood, including coronary circulation which drains into the right atrium, and that the right ventricle is unloaded to a greater extent. The use of multiple cannulas, however, consequently requires multiple cannula insertion sites, thereby increasing the risk of bleeding, vessel damage, and infection, as well as pain and discomfort to the patient.

While multi-lumen cannulas exist in the art, such cannulas may not be configured for draining blood flow from two separate sites. For example, certain known dual lumen cannula can be used to unload the right side of the heart by drawing blood from the right atrium through one lumen and infusing blood to the pulmonary artery through a second lumen. Another known VA ECMO system utilizes a dual lumen cannula in which both lumens are used for drainage to the pump. In such a system the lumens of the cannula are separated by a "Y" connector into two outlets, which must be rejoined by a separate connector element to create a single lumen of flow into the pump. Of the known medical devices and methods for VA ECMO, each has certain advantages and disadvantages. There is an ongoing need to provide alternative medical devices for VA ECMO as well as alternative methods for using the medical devices.

SUMMARY

This disclosure provides design, material, manufacturing method, and use alternatives for medical devices.

One example is a veno-arterial extracorporeal membrane oxygenation (VA ECMO) system. The system includes a dual lumen drainage cannula comprising a first drainage tube and a second drainage tube. The first drainage tube having a proximal end, a distal end, and a lumen extending therein. The first drainage tube includes at least one aperture defined proximate the distal end of the first drainage tube and in fluid communication with the lumen of the first drainage tube. The second drainage tube has a proximal end, a distal end, and a lumen extending therein. The second drainage tube includes at least one aperture defined proximate the distal end of the second drainage tube and in fluid communication with the lumen of the second drainage tube. The second drainage tube surrounds at least a portion of the first drainage tube. The dual lumen drainage cannula also includes a flow restrictor disposed within at least one of (a) the lumen of the first drainage tube proximal of the at least one aperture proximate the distal end of the first drainage tube and/or (b) the lumen of the second drainage tube proximal of the at least one aperture proximate the distal end of the second drainage tube. The dual lumen drainage cannula also includes an outlet fitting in fluid communication with the lumen of the first drainage tube and the lumen of the second drainage tube. The distal end of the second drainage tube is secured to a portion of the first drainage tube between the proximal and distal ends of the first drainage tube.

In addition or alternatively to any example above, the flow restrictor is an inflatable balloon.

In addition or alternatively to any example above, the inflatable balloon is disposed circumferentially around the first drainage tube and within the lumen of the second drainage tube.

In addition or alternatively to any example above, the inflatable balloon is toroid shaped.

In addition or alternatively to any example above, the dual lumen drainage cannula further includes an inflation lumen extending from the inflatable balloon proximally along the first drainage tube.

In addition or alternatively to any example above, the inflation lumen is embedded within a wall of the first drainage tube.

In addition or alternatively to any example above, the inflatable balloon is positioned in a proximal region of the second drainage tube, adjacent the outlet fitting.

In addition or alternatively to any example above, the inflatable balloon is disposed within the lumen of the first drainage tube.

In addition or alternatively to any example above, the inflatable balloon is attached to an inner surface of the second drainage tube, the inflatable balloon extending radially inward toward the first drainage tube when inflated.

In addition or alternatively to any example above, the flow restrictor is an expandable coil surrounding the first drainage tube.

In addition or alternatively to any example above, the outlet fitting comprises a single lumen in fluid communication with both the lumen of the first drainage tube and the lumen of the second drainage tube.

In addition or alternatively to any example above, the system further includes a blood pump having an inlet connected to the outlet fitting of the dual lumen drainage cannula, an oxygenator connected to an outlet of the blood pump, and an infusion cannula connected to an outlet of the oxygenator and configured for insertion into the vasculature of a patient.

In addition or alternatively to any example above, the first drainage tube extends coaxially through the lumen of the second drainage tube.

In addition or alternatively to any example above, the proximal end of the first drainage tube is positioned distally of the outlet fitting.

Another example is a dual lumen drainage cannula configured for use in a veno-arterial extracorporeal membrane oxygenation (VA ECMO) system. The dual lumen drainage cannula includes an inner drainage tube having a proximal end, a distal end, and a lumen extending therein. The inner drainage tube includes at least one aperture defined proximate the distal end of the inner drainage tube and in fluid communication with the lumen of the inner drainage tube. The dual lumen drainage cannula also includes an outer drainage tube having a proximal end, a distal end, and a lumen extending therein. The outer drainage tube includes at least one aperture defined proximate the distal end of the outer drainage tube and in fluid communication with the lumen of the outer drainage tube. The outer drainage tube is positioned coaxially around a portion of the inner drainage tube. The dual lumen drainage cannula also includes a flow restrictor disposed within the lumen of at least one of the inner and outer drainage tubes. The flow restrictor is configured to move between a first position in which flow through the lumen in which the flow restrictor is disposed is unrestricted, and a second position in which the flow restrictor is expanded to restrict flow through the lumen of the drainage tube in which the flow restrictor is disposed. The distal end of the outer drainage tube is secured to a portion of the inner drainage tube between the proximal and distal ends of the inner drainage tube.

In addition or alternatively to any example above, the flow restrictor is an inflatable balloon.

In addition or alternatively to any example above, the inflatable balloon is attached to an outer surface of the inner drainage tube, within the lumen of the outer drainage tube.

In addition or alternatively to any example above, the inflatable balloon is attached to an inner surface of the outer drainage tube.

In addition or alternatively to any example above, the inflatable balloon is attached to an inner surface of the inner drainage tube, within the lumen of the inner drainage tube.

Another example is a method of providing veno-arterial extracorporeal membrane oxygenation (VA ECMO) of a heart. The method includes providing a dual lumen drainage cannula. The dual lumen drainage cannula includes a first drainage tube and a second drainage tube. The first drainage tube has a proximal end, a distal end, a lumen extending therein, and at least one aperture defined proximate the distal end of the first drainage tube and in fluid communication with the lumen of the first drainage tube. The second drainage tube has a proximal end, a distal end, a lumen extending therein, and at least one aperture defined proximate the distal end of the second drainage tube and in fluid communication with the lumen of the second drainage tube. A flow restrictor is disposed within the lumen of the second drainage tube, proximal of the at least one aperture of the second drainage tube. The distal end of the second drainage tube is secured to a portion of the first drainage tube between the proximal and distal ends of the first drainage tube. The method includes inserting the dual lumen drainage cannula into a first site in a patient's vasculature and maneuvering the dual lumen drainage cannula through the patient's vasculature such that the distal end of the first drainage tube is at a first drainage location at least within proximity of the patient's pulmonary artery and such that the distal end of the second drainage tube is at a second drainage location at least within proximity of the patient's right atrium. Thereafter, the method includes draining blood through the first drainage tube and the second drainage tube to a blood pump. The method further includes pumping drained blood through an oxygenator to increase oxygen content and reduce carbon dioxide content of the drained blood, and delivering oxygenated blood to a second site in the patient's vasculature. A flow distribution between the first and second drainage locations is adjusted by inflating the inflatable balloon to increase resistance of blood flow within the lumen of the second drainage tube.

The above summary of some embodiments, aspects, and/or examples is not intended to describe each embodiment or every implementation of the present disclosure. Further details and advantages of the present disclosure will be understood from the following detailed description read in conjunction with the accompanying drawings.

Figure 1:
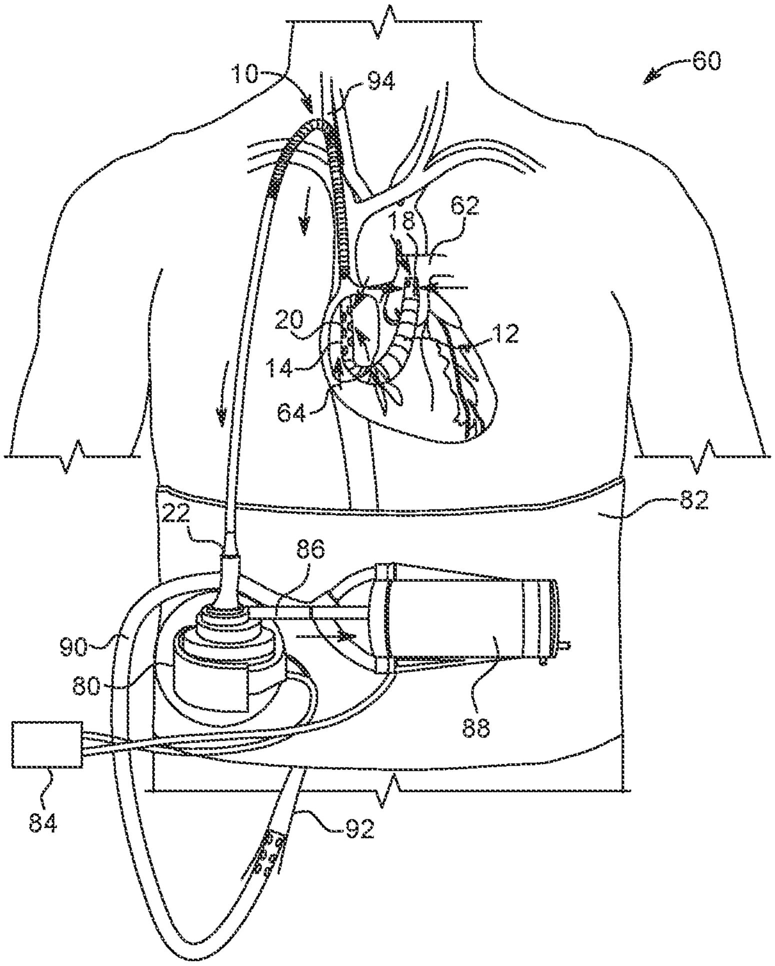
FIG. 1 is a schematic view of a VA ECMO system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For purposes of the description hereinafter, the terms "end," "upper," "lower," "right," "left," "vertical," "horizontal," "top," "bottom," "lateral," "longitudinal," and derivatives thereof shall relate to the orientation shown in the drawing figures. However, it is to be understood that embodiments of the present disclosure may assume various alternative variations and step sequences, except where expressly specified to the contrary. It is also to be understood that the specific devices and processes illustrated in the attached drawings, and described in the following specification, are simply exemplary embodiments or aspects. Hence, specific dimensions and other physical characteristics related to the embodiments or aspects disclosed herein are not to be considered as limiting.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F. When used in relation to a cannula, catheter, or other device inserted into a patient, the term "proximal" refers to a portion of such device farther from the end of the device inserted into the patient. When used in relation to a cannula, catheter, or other device inserted into a patient, the term "distal" refers to a portion of such device nearer to the end of the device inserted into the patient. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

An exemplary VA ECMO system is shown in FIG. 1, which illustrates a drainage cannula 10 inserted into the vasculature of a patient as part of a VA ECMO system 60. The cannula 10 includes a first drainage tube 12 positioned such that a plurality of apertures 18 therein is located in the pulmonary artery 62, thereby allowing blood from the pulmonary artery 62 to drain through the plurality of apertures 18 and into a lumen in the first drainage tube 12. A second drainage tube 14 is positioned such that a plurality of apertures 20 therein is located in the right atrium 64, thereby allowing blood from the right atrium 64 to drain through the plurality of apertures 20 and into a second lumen in the second drainage tube 14. An outlet fitting 22 of the drainage cannula 10 may be connected to an inlet fitting of a blood pump 80. The pump 80 can be any centrifugal, axial, mixed, or roller pump that can produce adequate flowrates through the system. Several examples of pumps include, without limitation the TANDEMHEART pump manufactured by CardiacAssist, Inc., the BIOMEDICUS pump manufactured by Medtronic, Inc., the ROTAFLOW pump manufactured by Jostra Medizintechnik AG, the CENTRIMAG pump manufactured by Levitronix, LLC, the SARNS DELPHIN pump manufactured by the Terumo Cardiovascular Group, the REVOLUTION pump manufactured by Cobe Cardiovascular, Inc, and others.

The pump 80 can be secured to the patient, for instance with a holster 82 that holds the pump 80 with a strap or in a pocket. The holster 82 can be wrapped around the abdomen or shoulder or leg of the patient. A controller 84 may be provided for controlling the operation of the pump 80. The controller 84 may be built into the pump 80. The pump 80 further includes an outlet 86 for delivering blood to an oxygenator 88. The oxygenator 88 may be secured to the holster 82. The pump outlet 86 may be directly connected to the oxygenator 88, or the pump outlet 86 may be indirectly connected to the oxygenator 88 via a conduit or hose. The oxygenator 88 may include an oxygenation membrane or other element(s) for oxygenating blood flowing through the oxygenator 88. Oxygenated blood is delivered to an artery in the patient's body through an infusion cannula 90. FIG. 1 illustrates the infusion cannula 90 connected to the outlet of the oxygenator 88 and connected to the patient's femoral artery 92.

The cannula 10 may be any dual lumen cannula. For example, the cannula 10 may be a dual lumen cannula such as is described in U.S. Pat. Nos. 9,168,352, 9,782,534, and 10,279,101, the disclosures of which are hereby incorporated by reference in their entireties. The cannula 10 may also be any of the various embodiments of drainage cannula 100, 200, 300, 400 as illustrated and described in further detail herein.

Referring to the drawings, in which like reference characters refer to like parts throughout the several views thereof, various embodiments of a dual lumen drainage cannula 100 (hereinafter referred to as "the drainage cannula 100") are shown. With initial reference to FIG. 2A, the assembled drainage cannula 100, according to one embodiment, generally includes an inner or first drainage tube 112 and an outer or second drainage tube 114. The first drainage tube 112 has a proximal end, a distal end, and a first length extending from the proximal end to the distal end. The second drainage tube 114 has a proximal end, a distal end, and a second length extending from the proximal end to the distal end. The first length of the first drainage tube 112 may be greater than the second length of the second drainage tube 114, such that the first drainage tube 112 extends distal of the distal end of the second drainage tube 114. In other words, the distal end of the first drainage tube 112 may be located distal of the distal end of the second drainage tube 114. The second drainage tube 114 may surround (e.g., coaxially surround) at least a portion of the first drainage tube 112, such that both the first drainage tube 112 and the second drainage tube 114 extend generally parallel to a central axis X-X. In some embodiments, the second drainage tube 114 may be arranged coaxially around the first drainage tube 112 and around the central axis X-X. The distal end of the second drainage tube 114 may be joined or secured to a portion of the first drainage tube 112 between the proximal and distal ends of the first drainage tube 112.

In some embodiments, a retainer 152 may extend radially outward from the first drainage tube 112 to position the first drainage tube 112 within the second drainage tube 114. In some embodiments, the retainer 152 may position the first drainage tube 112 so as to be coaxial with the second drainage tube 114. In some embodiments, the retainer 152 may be located at or near the proximal end of the first drainage tube 112. In some embodiments, a plurality of retainers 152 may be spaced along the length of the first drainage tube 112 to support or space the first drainage tube 112 relative to the second drainage tube 114 at a plurality of axial locations. In still other embodiments, the retainer 152 may extend axially along a portion of the length of the first drainage tube 112 or along the entire length of the first drainage tube 112.

An inner diameter of the second drainage tube 114 may be greater than an outer diameter of the first drainage tube 112 such that a flow cavity (i.e., lumen) 111 is formed inside the second drainage tube 114 between the inner surface of the second drainage tube 114 and the outer surface of the first drainage tube 112 disposed within the second drainage tube 114. The lumen of the first drainage tube 112 and the lumen of the second drainage tube 114 are fluidly separated from one another along the entire length of the first drainage tube 112, such that a first fluid (e.g. blood drained from the pulmonary artery of a patient) carried through the lumen of the first drainage tube 112 (arrow 133) does not mix with a second fluid (e.g. blood drained from the right atrium of the patient) carried through the lumen of the second drainage tube 114 (arrow 131) until the first fluid reaches a proximal end of the first drainage tube 112, at which point the lumen of the first drainage tube 112 may converge or be in fluid communication with the lumen of the second drainage tube 114.

One or both of the first drainage tube 112 and the second drainage tube 114 may be manufactured from a medical-grade material such as polyurethane. Alternatively, the tubes may be made from PVC or silicone, and may be dip molded, extruded, co-molded, or made using any other suitable manufacturing technique.

Figure 2A:
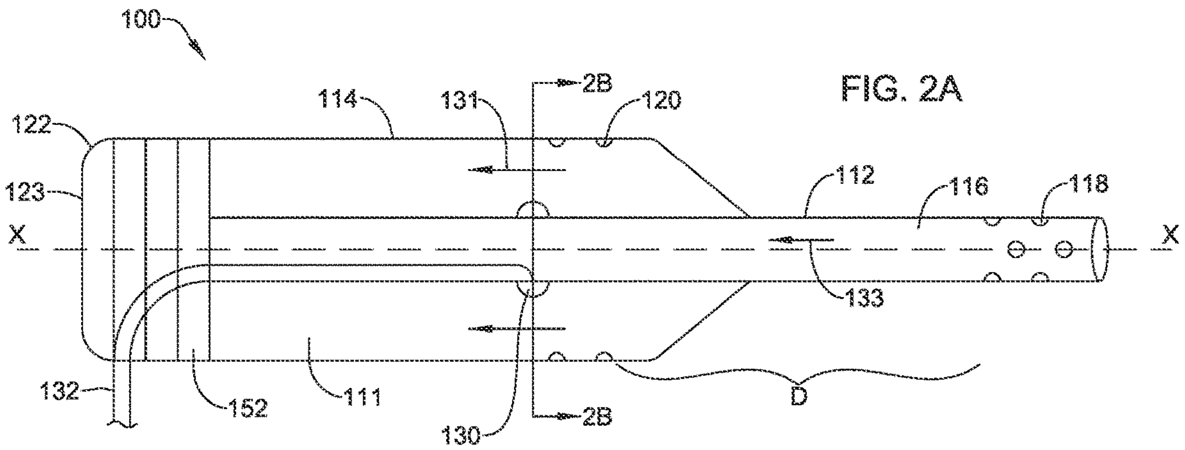
FIG. 2A is a side cross-sectional view of a drainage cannula according to an embodiment of the present disclosure.

With continued reference to FIG. 2A, at least one aperture 118 may be provided proximate a distal end of the first drainage tube 112, such as through a sidewall of the first drainage tube 112. The one or more apertures 118 may be located proximal of the distal end of the first drainage tube 112, but distal of the proximal end of the first drainage tube 112. In some embodiments, the at least one aperture 118 includes a plurality of apertures 118. The plurality of apertures 118 may be located proximal of the distal end of the first drainage tube 112 and distal of the proximal end of the first drainage tube 112. When more than one aperture 118 is present, the plurality of apertures 118 is desirably arranged in a circular pattern extending around a circumference of the first drainage tube 112 and extending through a sidewall of the first drainage tube 112 from an exterior of the first drainage tube 112 into the lumen of the first drainage tube 112. In some embodiments, the plurality of apertures 118 may be disposed in multiple groups provided at various sites on the first drainage tube 112.

Similarly, at least one aperture 120 may be provided proximate a distal end of the second drainage tube 114, such as through a sidewall of the second drainage tube 114. The one or more apertures 120 may be located proximal of the distal end of the second drainage tube 114, but distal of the proximal end of the second drainage tube 114. In some embodiments, the at least one aperture 120 includes a plurality of apertures 120. The plurality of apertures 120 may be located proximal of the distal end of the second drainage tube 114 and distal of the proximal end of the second drainage tube 114. When more than one aperture 120 is present, the plurality of apertures 120 is desirably arranged in a circular pattern extending around the outer circumference of the second drainage tube 114 and extending through a sidewall of the second drainage tube 114 from an exterior of the second drainage tube 114 into the lumen of the second drainage tube 114. In alternative embodiments, the plurality of apertures 120 may be arranged in groups disposed at various sites along the length of the second drainage tube 114. Blood may enter the first drainage tube 112 through the distal end and/or aperture(s) 118, and flow proximally through the lumen 116 of the first drainage tube 112, as indicated by arrow 133. Blood may enter the second drainage tube 114 through aperture(s) 120 and flow proximally through the lumen 111 of the second drainage tube 114, as indicated by arrow 131. The apertures 118 of the first drainage tube 112 may be separated along the length of the drainage cannula 100 from the apertures 120 of the second drainage tube 114 by a distance D. As shown in FIG. 2A, the distance D may be measured between the distalmost aperture 120 and the proximalmost aperture 118. In some embodiments the distance D may be, or may correspond to, a vascular distance between the right atrium and the pulmonary artery of the patient, for example D may be 15 cm to 25 cm, such that the drainage cannula 100, when positioned in a patient for a VA ECMO procedure, may drain blood from the pulmonary artery via the apertures 118 of the first drainage tube 112 and drain blood from the right atrium via the apertures 120 of the second drainage tube 114. The distance D may vary based on the age and size of the patient, as well as the desired flow rates during the VA ECMO procedure. In some embodiments, the distance D may be, or may correspond to, a vascular distance between the right ventricle and the pulmonary artery of the patient, for example D may be 12 cm to 22 cm, such that the drainage cannula 100, when positioned in a patient for a VA ECMO procedure, may drain blood from the pulmonary artery via the apertures 118 of the first drainage tube 112 and drain blood from the right ventricle via the apertures 120 of the second drainage tube 114. In yet other embodiments, the apertures 120 may be positioned so as to drain blood from both the right atrium and the right ventricle simultaneously.

With continuing reference to FIG. 2A, an outlet fitting 122 may be provided at the proximal end of the drainage cannula 100 for connecting the drainage cannula 100 to other medical devices, such as a blood pump 80 (see FIG. 1). The drainage cannula 100 may be connected to other elements of a VA ECMO system, such as the oxygenator 88 and/or infusion cannula 90 described above with reference to FIG.

1. The outlet fitting 122 may be in fluid communication with the lumen of the first drainage tube 112 and the lumen of the second drainage tube 114 such that the drainage cannula 100 defines only a single outlet for draining fluid from both the first drainage tube 112 and the second drainage tube 114. In particular, the outlet fitting 122 defines a single outlet lumen 123 in fluid communication with the lumen of the first drainage tube 112 and the lumen of the second drainage tube 114 such that all flow in a proximal direction out of the drainage cannula 100 must flow through the single outlet lumen 123. The proximal end of the first drainage tube 112 may be positioned distally of the outlet fitting 122. The outlet fitting 122 may be, for example, a male hose barb, a luer connector, a male or female threaded connector, or a continuation of the second drainage tube 114 configured to fit over a hose barb, for example. Other configurations are also contemplated.

With continuing reference to FIG. 2A, a flow restrictor 130 may be provided within the lumen of at least one of the first and second drainage tubes 112, 114, proximal of the aperture(s) 118, 120 in the distal end of the drainage tube in which the flow restrictor 130 resides. In the embodiment illustrated in FIG. 2A, the flow restrictor 130 is disposed within the lumen 111 of the second drainage tube 114. The flow restrictor 130 may allow a physician or other user to reduce the cross-sectional area of the lumen 111 as a way of controlling fluid flow through the second drainage tube 114, and thereby to control the ratio of volume and/or flow rate of fluid drained from the first drainage tube 112 relative to the volume and/or flow rate of fluid drained from the second drainage tube 114. Without modulating the flow through the second drainage tube 114, most of the total flow may come from the right atrium, which may leave stagnant blood in the pulmonary artery lumen and in the pulmonary artery around the cannula, which may result in blood clots. The flow restrictor 130 may be expandable to any one of a plurality of sizes to provide a varying reduction in the cross-sectional area of the lumen 111, thus restricting the flow rate of blood through the lumen 111. For example, the flow restrictor 130 may be configured to expand to restrict 5-100%, 10-100%, 20-100%, 50%-100%, 5%-90%, or 10-90% of the cross-sectional area of the lumen 111. In some embodiments, the flow restrictor 130 may be expandable to restrict 10% or more, 20% or more, 30% or more, 40% or more, 50% or more, 60% or more, 70% or more, or 80% or more of the cross-sectional area of the lumen 111. In some instances, the flow restrictor 130 may be expandable to restrict 10-100%, 10-95%, 10-90%, 10-80%, 10-70%, 10-50%, 10-25%, 15-100%, 15-90%, 15-70%, 15-60%, 25-100%, 25-90%, 25-70%, 25-50%, 30-100%, 30-90%, 30-60%, 50-100% or 70-100% of the cross-sectional area of the lumen 111.

In the embodiment illustrated in FIGS. 2A-4B, the flow restrictor is an inflatable balloon 130. An inflation lumen 132 may extend from the inflatable balloon 130, along the outer wall of the first drainage tube 112 to or toward the proximal end of the first drainage tube 112. In some instances, the inflation lumen 132 may extend through the outlet fitting 122. In other embodiments, the inflation lumen 132 may be embedded or extruded within the outer wall of the first drainage tube 112. In some embodiments, the inflatable balloon 130 may be fixed to the outer surface of the first drainage tube 112. The inflatable balloon 130 may generally be positioned proximal of the plurality of apertures 120 in the second drainage tube 114. In some embodiments, the inflatable balloon 130 may be positioned in a proximal region of the second drainage tube 114, adjacent the outlet fitting 122. The inflatable balloon 130 may be toroid shaped, cylindrical, circular, half-moon shaped, or any other shape that, when expanded, reduces the cross-sectional area of the lumen 111. In some instances, the inflatable balloon 130 may extend circumferentially around the entire circumference of the first drainage tube 112, as illustrated in the cross-sectional view of FIG. 2B.

Figure 2B:
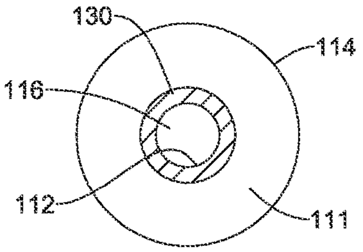
FIG. 2B is a cross-sectional view of FIG. 2A, taken along line 2B-2B.
Figure 3A:
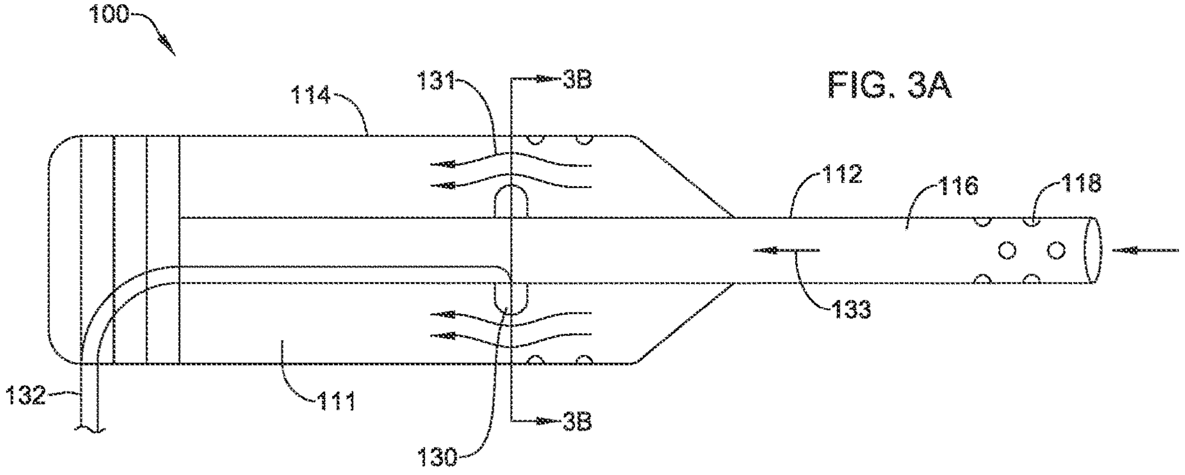
FIG. 3A is a side cross-sectional view of the drainage cannula of FIG. 2A with the balloon partially inflated.
Figure 3B:
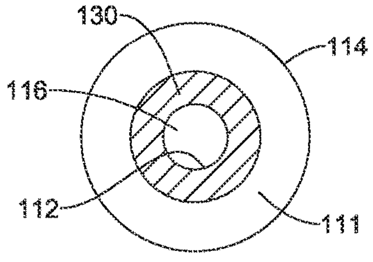
FIG. 3B is a cross-sectional view of the drainage cannula of FIG. 3A taken along line 3B-3B of FIG. 3A.
Figure 4A:
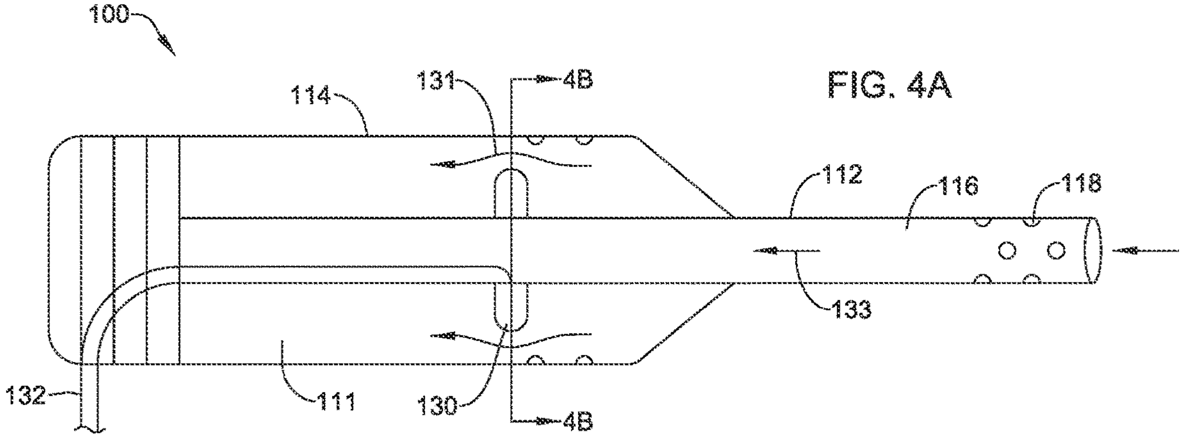
FIG. 4A is a side cross-sectional view of the drainage cannula of FIG. 2A with the balloon fully inflated.
Figure 4B:
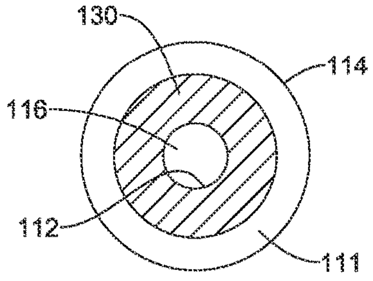
FIG. 4B is a cross-sectional view of the drainage cannula of FIG. 4A taken along line 4B-4B.

The inflatable balloon 130 may have a variety of configurations. In a first deflated configuration, as shown in FIGS. 2A and 2B, the inflatable balloon 130 may be completely deflated and flow through the lumen 111 between the first and second drainage tubes 112, 114, indicated by arrow 131, is unrestricted. Thus blood may flow through the lumen 111 at a first flow rate. In a second configuration, as shown in FIGS. 3A and 3B, the inflatable balloon 130 is partially expanded to partially restrict flow through the lumen 111, thus reducing the flow rate through the lumen 111 to a second flow rate, less than the first flow rate. In a third configuration, as shown in FIGS. 4A and 4B, the inflatable balloon 130 is fully expanded to further restrict flow through the lumen 111, thus further reducing the flow rate through the lumen 111 to a second flow rate, less than the first and second flow rates. The inflatable balloon 130 may be configured to be inflated to a variety of inflation states, providing a variable restriction of the lumen 111. In some examples, the inflatable balloon 130 may be inflatable to provide a 5-90% or 5-100% restriction of the cross-sectional area of the lumen 111, as desired, based on the amount of inflation fluid introduced into the inflatable balloon 130. For example, the flow restrictor, such as in the form of an inflatable balloon 130, may be configured to expand to restrict 5-100%, 10-100%, 20-100%, 50%-100%, 5%-90%, or 10-90% of the cross-sectional area of the lumen 111. In some embodiments, the flow restrictor, in the form of an inflatable balloon 130, may be expandable to restrict 10% or more, 20% or more, 30% or more, 40% or more, 50% or more, 60% or more, 70% or more, or 80% or more of the cross-sectional area of the lumen 111. In some instance, the flow restrictor, in the form of an inflatable balloon 130, may be expandable to restrict 10-100%, 10-95%, 10-90%, 10-80%, 10-70%, 10-50%, 10-25%, 15-100%, 15-90%, 15-70%, 15-60%, 25-100%, 25-90%, 25-70%, 25-50%, 30-100%, 30-90%, 30-60%, 50-100% or 70-100% of the cross-sectional area of the lumen 111. In other embodiments, the inflatable balloon 130 may provide a smaller range of restriction, such as 5-50%. Other ranges of restriction, such as those provided above, are also contemplated.

In another embodiment, a drainage cannula 200 may have an inner or first drainage tube 212 with a plurality of apertures 218 in a distal end thereof, such as extending through a sidewall thereof, and an outer or second drainage tube 214 with a plurality of apertures 220 in a distal end thereof, such as extending through a sidewall thereof, similar to the drainage cannula 100 described above. The second drainage tube 214 may be arranged coaxially around the first drainage tube 212, or otherwise surround the first drainage tube 212, and the distal end of the second drainage tube 214 may be joined or secured to a portion of the first drainage tube 212 between the proximal and distal ends of the first drainage tube 212.

Figure 5A:
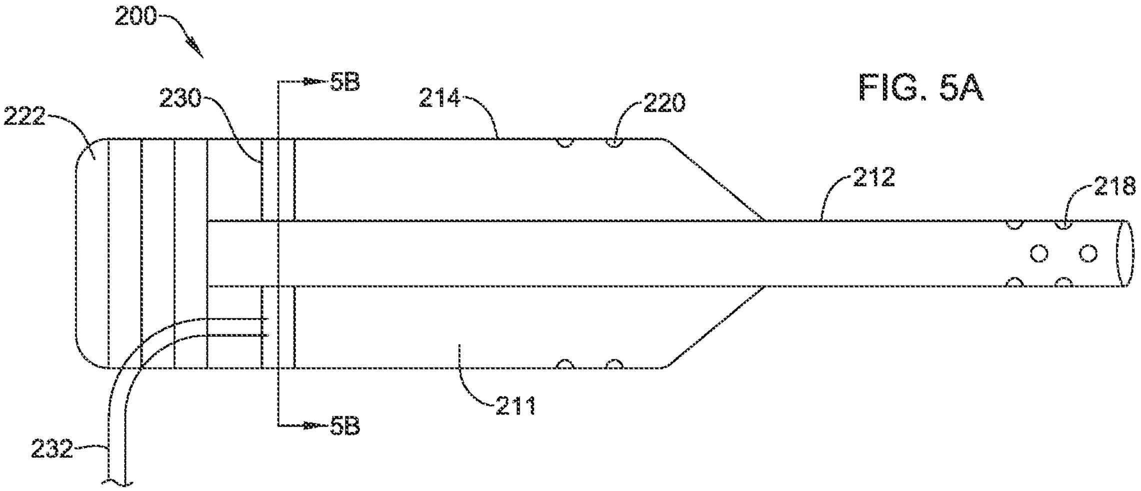
FIG. 5A is a side cross-sectional view of another drainage cannula according to an embodiment of the present disclosure.
Figure 5B:
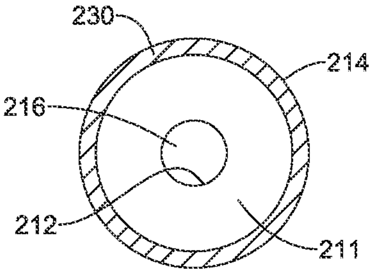
FIG. 5B is a cross-sectional view of the drainage cannula of FIG. 5A in a deflated configuration, taken along line 5B-5B.
Figure 5C:
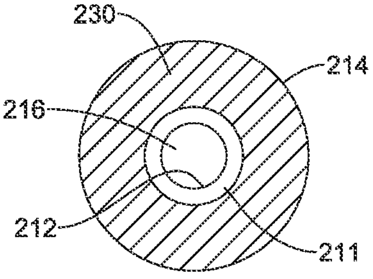
FIG. 5C is a cross-sectional view of the drainage cannula of FIG. 5A in a fully inflated configuration, taken along line 5B-5B.

In the embodiment illustrated in FIGS. 5A-5C, a flow restrictor in the form of an inflatable balloon 230 is disposed within the lumen 211 of the second drainage tube 214, attached to the inner surface of the second drainage tube 214. An inflation lumen 232 may extend from the inflatable balloon 230, along the inner wall of the second drainage tube 214, to or toward the proximal end of the second drainage tube 214. In some instances, the inflation lumen 232 may extend through the outlet fitting 222. The inflatable balloon 230 may be positioned in a proximal region of the second drainage tube 214, adjacent the outlet fitting 222. The inflatable balloon 230 may be toroid shaped, cylindrical, circular, half-moon shaped, or any other shape that, when expanded, extends toward the first drainage tube 212, reducing the cross-sectional area of the lumen 211. The inflatable balloon 230 may extend circumferentially around the entire circumferential inner surface of the second drainage tube 214, as illustrated in the cross-sectional view of FIG. 5B.

The inflatable balloon 230 may have a variety of configurations. In a first deflated configuration, as shown in FIG. 5B, the inflatable balloon 230 may be completely deflated and flow through the lumen 211 between the first and second drainage tubes 212, 214 is unrestricted. Thus blood may flow through the lumen 211 at a first flow rate. As the inflatable balloon 230 is inflated to the fully expanded configuration, as shown in FIG. 5C, the flow through the lumen 211 is increasingly restricted, thus reducing the flow rate of the blood through the lumen 211. In some examples, the inflatable balloon 230 may be inflatable to provide a 5-90% or 5-100% restriction of the cross-sectional area of the lumen 211, as desired, based on the amount of inflation fluid introduced into the inflatable balloon 230. For example, the flow restrictor, such as in the form of an inflatable balloon 230, may be configured to expand to restrict 5-100%, 10-100%, 20-100%, 50%-100%, 5%-90%, or 10-90% of the cross-sectional area of the lumen 211. In some embodiments, the flow restrictor, in the form of an inflatable balloon 230, may be expandable to restrict 10% or more, 20% or more, 30% or more, 40% or more, 50% or more, 60% or more, 70% or more, or 80% or more of the cross-sectional area of the lumen 211. In some instances, the flow restrictor, in the form of an inflatable balloon 230, may be expandable to restrict 10-100%, 10-95%, 10-90%, 10-80%, 10-70%, 10-50%, 10-25%, 15-100%, 15-90%, 15-70%, 15-60%, 25-100%, 25-90%, 25-70%, 25-50%, 30-100%, 30-90%, 30-60%, 50-100% or 70-100% of the cross-sectional area of the lumen 211. In other embodiments, the inflatable balloon 230 may provide a smaller range of restriction, such as 5-50%. Other ranges of restriction, such as those provided above, are also contemplated.

Figure 6A:
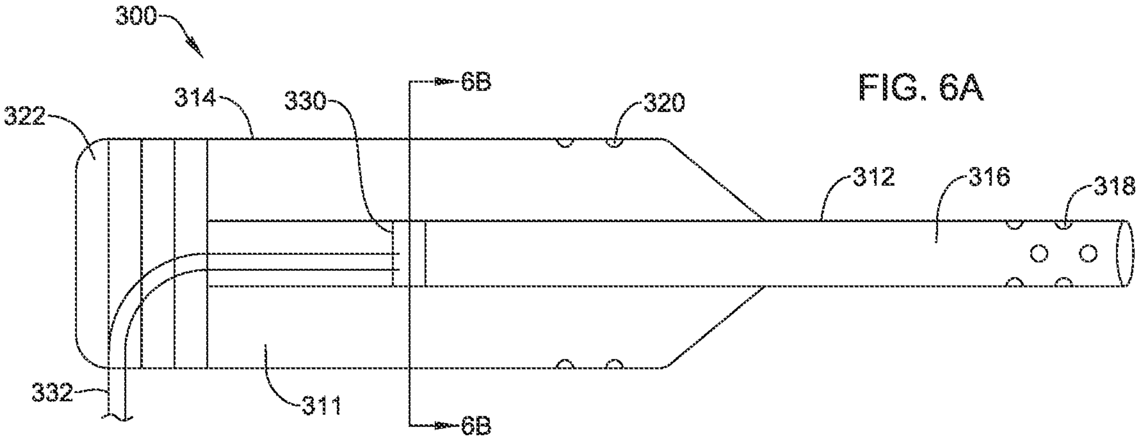
FIG. 6A is a side cross-sectional view of another drainage cannula according to an embodiment of the present disclosure.
Figure 6B:
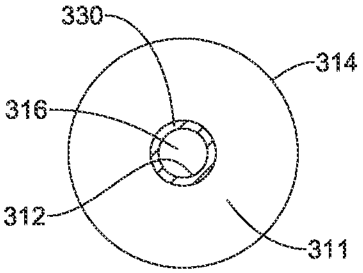
FIG. 6B is a cross-sectional view of the drainage cannula of FIG. 6A in a deflated configuration, taken along line 6B-6B.
Figure 6C:
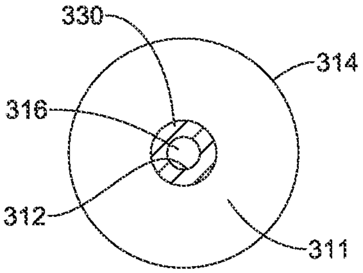
FIG. 6C is a cross-sectional view of the drainage cannula of FIG. 6A in a fully inflated configuration, taken along line 6B-6B.

Another embodiment of a drainage cannula 300 is illustrated in FIGS. 6A-6C. Similar to the drainage cannulas 100, 200, the drainage cannula 300 may have an inner or first drainage tube 312 with a plurality of apertures 318 in a distal end thereof, such as extending through a sidewall thereof, and an outer or second drainage tube 314 with a plurality of apertures 320 in a distal end thereof, such as extending through a sidewall thereof. The second drainage tube 314 may be arranged coaxially around the first drainage tube 312, or otherwise surround the first drainage tube 312, and the distal end of the second drainage tube 314 may be joined or secured to a portion of the first drainage tube 312 between the proximal and distal ends of the first drainage tube 312.

In the embodiment illustrated in FIGS. 6A-6C, a flow restrictor in the form of an inflatable balloon 330 is disposed within the lumen 316 of the first drainage tube 312, such as attached to the inner surface of the first drainage tube 312. An inflation lumen 332 may extend from the inflatable balloon 330, along the inner wall of the first drainage tube 312, to or toward the proximal end of the first drainage tube 312. In some instances, the inflation lumen 332 may extend through the outlet fitting 322. The inflatable balloon 330 may be positioned at any position proximal of the apertures 318 in the first drainage tube 312. The inflatable balloon 330 may be toroid shaped, cylindrical, circular, half-moon shaped, or any other shape that, when expanded, extends further into the lumen of the first drainage tube 312, reducing the cross-sectional area of the lumen 316. The inflatable balloon 330 may extend circumferentially around the entire circumferential inner surface of the first drainage tube 312, as illustrated in the cross-sectional view of FIG. 6B.

The inflatable balloon 330 may have a variety of configurations. In a first deflated configuration, as shown in FIG. 6B, the inflatable balloon 330 may be completely deflated and flow through the lumen 316 of the first drainage tube 312 is unrestricted. Thus blood may flow through the lumen 316 at a first flow rate. As the inflatable balloon 330 is inflated to the fully expanded configuration, as shown in FIG. 6C, the flow through the lumen 316 is increasingly restricted, thus reducing the flow rate of the blood through the lumen 316. In some examples, the inflatable balloon 330 may be inflatable to provide a 5-90% or 5-100% restriction of the cross-sectional area of the lumen 316, as desired, based on the amount of inflation fluid introduced into the inflatable balloon 330. For example, the flow restrictor, such as in the form of an inflatable balloon 330, may be configured to expand to restrict 5-100%, 10-100%, 20-100%, 50%-100%, 5%-90%, or 10-90% of the cross-sectional area of the lumen 316. In some embodiments, the flow restrictor, in the form of an inflatable balloon 330, may be expandable to restrict 10% or more, 20% or more, 30% or more, 40% or more, 50% or more, 60% or more, 70% or more, or 80% or more of the cross-sectional area of the lumen 316. In some instances, the flow restrictor, in the form of an inflatable balloon 330, may be expandable to restrict 10-100%, 10-95%, 10-90%, 10-80%, 10-70%, 10-50%, 10-25%, 15-100%, 15-90%, 15-70%, 15-60%, 25-100%, 25-90%, 25-70%, 25-50%, 30-100%, 30-90%, 30-60%, 50-100% or 70-100% of the cross-sectional area of the lumen 316. In other embodiments, the inflatable balloon 330 may provide a smaller range of restriction, such as 5-50%. Other ranges of restriction, such as those provided above, are also contemplated.

In some embodiments, the drainage cannula may include a first inflation balloon in the first drainage tube, as shown in any of FIGS. 2A-5C, and a second inflation balloon in the second drainage tube, as shown in FIGS. 6A-6C.

Figure 7:
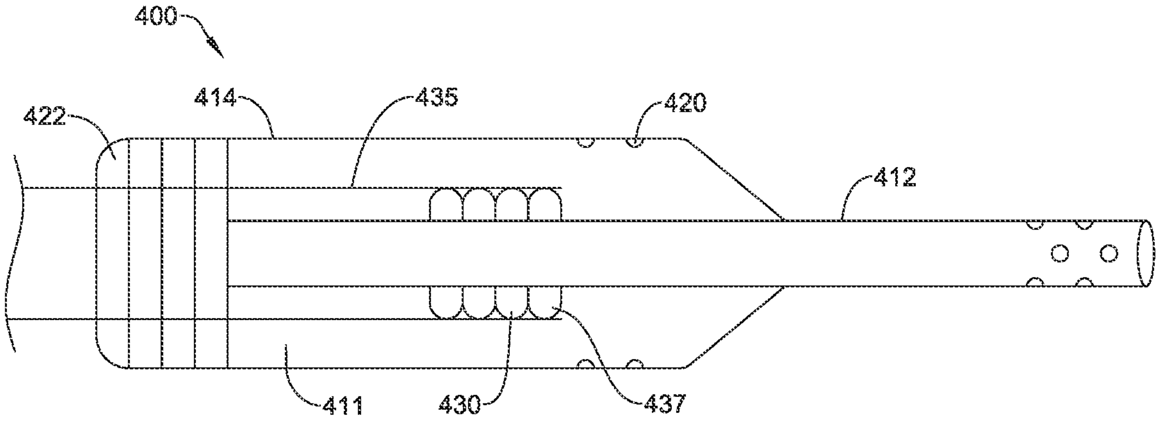
FIG. 7 is a side cross-sectional view of another drainage cannula according to an embodiment of the present disclosure.

In the embodiment illustrated in FIG. 7, a flow restrictor in the form of an expandable coil 430 is disposed around (i.e., surrounds) the first drainage tube 412, within the lumen 411 of the second drainage tube 414 defined between the outer surface of the first drainage tube 412 and the inner surface of the second drainage tub 414. The expandable coil 430 may be positioned proximal of the apertures 420 in the second drainage tube 414. The expandable coil 430 may be made of a flexible material, such as a superelastic material (e.g., nitinol). In some instances, the expandable coil 430 may be made of a shape memory material, such as nitinol or a shape memory polymer, configured to radially expand, thereby reducing the cross-sectional area of the lumen 411, and thus restricting blood flow through the lumen 411. An actuator, may extend through the lumen 411 and engage the coil 430 in order to selectively radially constrain and/or radially expand the coil 430. One example actuator, shown as an intermediate shaft 435, may extend through the lumen 411 between the first drainage tube 412 and the second drainage tube 414 and surround the coil 430 in order to cover and radially constrain the coil 430 until it is desired for the coil 430 to be expanded. The intermediate shaft 435 may be withdrawn proximally, such as through the outlet fitting 422, to release the coil, allowing the coil 430 to radially expand into the lumen 411. In other instances, an actuator, such as a plunger, may engage the coil 430 to axially compress the coil 430 in order to radially expand the coil 430. For example, the actuator (e.g., plunger) may engage the proximal end of the coil 430 to selectively axially compress the coil 430, and thereby radially expand the coil 430 to restrict blood flow around the coil 430 through the lumen 411. In some examples, the coil 430 may be radially expandable to provide a 5-90% or 5-100% restriction of the cross-sectional area of the lumen 411, as desired, based on the amount of radial expansion of the coil 430. For example, the flow restrictor, such as in the form of the coil 430, may be configured to expand to restrict 5-100%, 10-100%, 20-100%, 50%-100%, 5%-90%, or 10-90% of the cross-sectional area of the lumen 411. In some embodiments, the flow restrictor, in the form of the coil 430, may be expandable to restrict 10% or more, 20% or more, 30% or more, 40% or more, 50% or more, 60% or more, 70% or more, or 80% or more of the cross-sectional area of the lumen 411. In some instances, the flow restrictor, in the form of the coil 430, may be expandable to restrict 10-100%, 10-95%, 10-90%, 10-80%, 10-70%, 10-50%, 10-25%, 15-100%, 15-90%, 15-70%, 15-60%, 25-100%, 25-90%, 25-70%, 25-50%, 30-100%, 30-90%, 30-60%, 50-100% or 70-100% of the cross-sectional area of the lumen 411. In other embodiments, the coil 430 may provide a smaller range of restriction, such as 5-50%. Other ranges of restriction, such as those provided above, are also contemplated.

In some embodiments, the coil 430 may be covered with an impermeable membrane 437 to further restrict the flow through the lumen 411. The coil 430 may extend circumferentially around the first drainage tube 412. In other embodiments, the coil 430 may be made of a temperature-reactive material, such that the coil 430 expands upon insertion into the body or coming into contact with the patient's blood. In other embodiments, the coil 430 may be configured to expand when subjected or exposed to another stimuli. The coil 430 may be formed of any desired material, such as a metallic or polymeric material.

Having described several non-limiting embodiments of the drainage cannula 100, 200, 300, 400, an exemplary and non-limiting method for supporting the right heart of a patient using the drainage cannula 100, 200, 300, 400 will now be described. For simplicity, the drainage cannula 100 will be referred to, however it will be understood that the method may be performed with drainage cannula 200, 300, or 400 as well.

In use, the drainage cannula 100 may be inserted into a first site in the patient's vasculature, and maneuvered through the patient's vasculature such that the distal end of the first drainage tube 112 is at a first drainage location at least within proximity of the pulmonary artery and the distal end of the second drainage tube 114 is at a second drainage location at least within proximity of the patient's right atrium. The distal end of the first drainage tube 112 may be sufficiently flexible about the central axis X-X so as to navigate the internal jugular vein, right ventricle, and pulmonary artery. The drainage cannula 100 may include insertion depth markers and/or radiopaque markers for aiding the user in placing the drainage cannula 100 in the right atrium. Once the position of the drainage cannula 100 reaches a desired location, the drainage cannula 100 may be clamped in place. For example, the drainage cannula 100 may be secured to the patient's neck using a suture. In particular, the distal end of the second drainage tube 114 is positioned at least within proximity with the right atrium, while the distal end of the first drainage tube 112 extends into the pulmonary artery. With the drainage cannula 100 in the desired location, the flow restrictor 130 may be adjusted to achieve a desired flow rate through the cannula 100. In particular, the level of restriction of the cross-sectional area of the lumen 111 may be adjusted (e.g., by selectively inflating/deflating the flow restrictor 130) to achieve a desired flow rate through the lumen of the second drainage tube 114, thereby adjusting the ratio of volume and/or flow rate of fluid drained from the first drainage tube 112 relative to the volume and/or flow rate of fluid drained from the second drainage tube 114. When the flow restrictor 130 is an inflatable balloon, inflation media may be directed through the inflation lumen 132 to inflate the balloon 130 to a size corresponding to the desired percentage of restriction of the lumen 111 and/or achieving the desired volume and/or flow rate of fluid through the lumen 111. The amount of inflation media may be increased or decreased to adjust the size of the balloon 130 (and thus the amount of restriction of the lumen 111) during the procedure as needed to adjust the flow rate.

In some instances the VA ECMO system may include one or more sensors, such as flow sensors, communicating with a controller. In some instances the one or more sensors may be used to measure and communicate a parameter (e.g., flow rate, pressure, etc.) to the controller. In some instances the one or more sensors may be configured to communicate with the controller to automatically increase/decrease the restriction of the flow of blood through one of the lumens of the dual drainage cannula. For example, the controller of the VA ECMO system may automatically adjust (e.g., increase/decrease) the inflation pressure of the inflatable balloon 130, 230, 330 to provide a desired occlusion of the lumen within which the balloon 130, 230, 330 is positioned, thus controlling the flow rate of blood through the lumen.

In the VA ECMO system, the drainage cannula 100 allows blood to be drained through the first drainage tube 112 and the second drainage tube 114 to a blood pump. The drained blood may then be pumped through an oxygenator to increase oxygen content and reduce carbon dioxide content of the blood. The oxygenated blood may then be delivered with reduced carbon dioxide content to a second site in the patient's vasculature. The flow distribution between the first and second drainage locations may be adjusted by inflating the inflatable balloon to increase resistance within the second drainage tube.

While several embodiments of a drainage cannula are shown in the accompanying figures and described hereinabove in detail, other embodiments will be apparent to, and readily made by, those skilled in the art without departing from the scope and spirit of the embodiments of the present disclosure. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A veno-arterial extracorporeal membrane oxygenation (VA ECMO) system comprising:

a dual lumen drainage cannula comprising:

a first drainage tube having a proximal end, a distal end, and a lumen extending therein, the first drainage tube including at least one aperture defined proximate the distal end of the first drainage tube and in fluid communication with the lumen of the first drainage tube;

a second drainage tube having a proximal end, a distal end, and a lumen extending therein, the second drainage tube including at least one aperture defined proximate the distal end of the second drainage tube and in fluid communication with the lumen of the second drainage tube, the second drainage tube surrounding at least a portion of the first drainage tube;

a toroid shaped flow restrictor fixed to a lumen wall within at least one of:

(a) the lumen of the first drainage tube proximal of the at least one aperture proximate the distal end of the first drainage tube;

(b) the lumen of the second drainage tube proximal of the at least one aperture proximate the distal end of the second drainage tube; and an outlet fitting in fluid communication with the lumen of the first drainage tube and the lumen of the second drainage tube;

wherein the flow restrictor is configured to reduce a flow rate of fluid through the lumen of the first or second drainage tube, wherein the flow restrictor is adjustable while the dual lumen drainage cannula is in use to vary a cross-sectional area of the lumen of the first or second drainage cannula to vary the reduction in flow rate;

wherein the distal end of the second drainage tube is secured to a portion of the first drainage tube between the proximal and distal ends of the first drainage tube.

2. The VA ECMO system according to claim 1, wherein the flow restrictor is an inflatable balloon.

3. The VA ECMO system according to claim 2, wherein the inflatable balloon is disposed circumferentially around the first drainage tube and within the lumen of the second drainage tube.

4. The VA ECMO system according to claim 3, further comprising an inflation lumen extending from the inflatable balloon proximally along the first drainage tube.

5. The VA ECMO system according to claim 4, wherein the inflation lumen is embedded within a wall of the first drainage tube.

6. The VA ECMO system according to claim 3, wherein the inflatable balloon is positioned in a proximal region of the second drainage tube, adjacent the outlet fitting.

7. The VA ECMO system according to claim 2, wherein the inflatable balloon is disposed within the lumen of the first drainage tube.

8. The VA ECMO system according to claim 2, wherein the inflatable balloon is attached to an inner surface of the second drainage tube, the inflatable balloon extending radially inward toward the first drainage tube when inflated.

9. The VA ECMO system according to claim 1, wherein the flow restrictor is an expandable coil surrounding the first drainage tube.

10. The VA ECMO system according to claim 1, wherein the outlet fitting comprises a single lumen in fluid communication with both the lumen of the first drainage tube and the lumen of the second drainage tube.

11. The VA ECMO system according to claim 1, further comprising:

a blood pump having an inlet connected to the outlet fitting of the dual lumen drainage cannula;

an oxygenator connected to an outlet of the blood pump; and an infusion cannula connected to an outlet of the oxygenator and configured for insertion into the vasculature of a patient.

12. The VA ECMO system according to claim 1, wherein the first drainage tube extends coaxially through the lumen of the second drainage tube.

13. The VA ECMO system according to claim 1, wherein the proximal end of the first drainage tube is positioned distally of the outlet fitting.

14. A dual lumen drainage cannula configured for use in a veno-arterial extracorporeal membrane oxygenation (VA ECMO) system, the dual lumen drainage cannula comprising:

an inner drainage tube having a proximal end, a distal end, and a lumen extending therein, the inner drainage tube including at least one aperture defined proximate the distal end of the inner drainage tube and in fluid communication with the lumen of the inner drainage tube;

an outer drainage tube having a proximal end, a distal end, and a lumen extending therein, the outer drainage tube including at least one aperture defined proximate the distal end of the outer drainage tube and in fluid communication with the lumen of the outer drainage tube, the outer drainage tube positioned coaxially around a portion of the inner drainage tube; and a toroid shaped flow restrictor fixed to a lumen wall within the lumen of at least one of the inner and outer drainage tubes, the flow restrictor configured to move between a first position in which flow through the lumen in which the flow restrictor is disposed is unrestricted, and at least a second position in which the flow restrictor is at least partially expanded to restrict flow through the lumen of the drainage tube in which the flow restrictor is disposed, wherein the flow restrictor is configured to move back and forth between the first and second positions during use to vary a cross-sectional area of the lumen of the drainage tube in which the flow restrictor is disposed, and to vary the reduction in flow rate during use;

wherein the distal end of the outer drainage tube is secured to a portion of the inner drainage tube between the proximal and distal ends of the inner drainage tube.

15. The dual lumen drainage cannula according to claim 14, wherein the flow restrictor is an inflatable balloon.

16. The dual lumen drainage cannula according to claim 15, wherein the inflatable balloon is attached to an outer surface of the inner drainage tube, within the lumen of the outer drainage tube.

17. The dual lumen drainage cannula according to claim 15, wherein the inflatable balloon is attached to an inner surface of the outer drainage tube.

18. The dual lumen drainage cannula according to claim 15, wherein the inflatable balloon is attached to an inner surface of the inner drainage tube, within the lumen of the inner drainage tube.

19. A method of providing veno-arterial extracorporeal membrane oxygenation (VA ECMO) of a heart, the method comprising:

providing a dual lumen drainage cannula comprising:

a first drainage tube having a proximal end, a distal end, a lumen extending therein, and at least one aperture defined proximate the distal end of the first drainage tube and in fluid communication with the lumen of the first drainage tube;

a second drainage tube having a proximal end, a distal end, a lumen extending therein, and at least one aperture defined proximate the distal end of the second drainage tube and in fluid communication with the lumen of the second drainage tube; and a flow restrictor fixed to a lumen wall within the lumen of the second drainage tube, proximal of the at least one aperture of the second drainage tube, wherein the flow restrictor is a toroid shaped inflatable balloon and is adjustable to vary a flow rate of blood through the lumen of the second drainage tube;

wherein the distal end of the second drainage tube is secured to a portion of the first drainage tube between the proximal and distal ends of the first drainage tube;

inserting the dual lumen drainage cannula into a first site in a patient's vasculature;

maneuvering the dual lumen drainage cannula through the patient's vasculature such that the distal end of the first drainage tube is at a first drainage location at least within proximity of the patient's pulmonary artery and such that the distal end of the second drainage tube is at a second drainage location at least within proximity of the patient's right atrium;

draining blood through the first drainage tube and the second drainage tube to a blood pump;

pumping drained blood through an oxygenator to increase oxygen content and reduce carbon dioxide content of the drained blood;

delivering oxygenated blood to a second site in the patient's vasculature; and adjusting a flow distribution between the first and second drainage locations during use of the dual lumen drainage cannula by inflating the inflatable balloon to reduce a cross-sectional area of the lumen of the second drainage tube but not block the lumen, and increase resistance of blood flow within the lumen of the second drainage tube.

* * * * *